US007021311B2

(12) United States Patent
Gunaratnam et al.

(10) Patent No.: US 7,021,311 B2
(45) Date of Patent: Apr. 4, 2006

(54) MASK CUSHION AND FRAME ASSEMBLY

(75) Inventors: Michael K. Gunaratnam, Marsfield (AU); Gregory S. Smart, Randwick (AU); Philip R. Kwok, Chetawood (AU)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 10/751,926

(22) Filed: Jan. 7, 2004

(65) Prior Publication Data

US 2004/0134497 A1 Jul. 15, 2004

Related U.S. Application Data

(60) Division of application No. 10/123,484, filed on Apr. 17, 2002, now Pat. No. 6,796,308, which is a continuation of application No. 09/501,004, filed on Feb. 9, 2000, now Pat. No. 6,412,487, which is a continuation-in-part of application No. 09/498,705, filed on Feb. 7, 2000, now Pat. No. 6,491,034, and a continuation-in-part of application No. 29/115,618, filed on Dec. 16, 1999, now Pat. No. Des. 443,355, and a continuation-in-part of application No. 09/316,227, filed on May 21, 1999, now Pat. No. 6,513,526, and a continuation-in-part of application No. 29/101,860, filed on Mar. 12, 1999, now Pat. No. Des. 428,139, and a continuation-in-part of application No. 29/101, 861, filed on Mar. 12, 1999, now Pat. No. Des. 430,663, and a continuation-in-part of application No. 29/101,862, filed on Mar. 12, 1999, now Pat. No. Des. 428,988.

(30) Foreign Application Priority Data

| | | |
|---|---|---|
| Dec. 9, 1998 | (AU) | 3922/1998 |
| Dec. 9, 1998 | (AU) | 3923/1998 |
| Dec. 9, 1998 | (AU) | 3924/1998 |
| Feb. 9, 1999 | (AU) | PP8550 |
| Jun. 18, 1999 | (AU) | 1916/99 |
| Jun. 18, 1999 | (AU) | PQ1029 |
| Jun. 18, 1999 | (AU) | PQ1040 |

(51) Int. Cl.
*A62B 18/08* (2006.01)

(52) U.S. Cl. ............................ 128/206.24; 128/205.25

(58) Field of Classification Search .................. 24/459, 24/518, 543; 128/205.25, 206.24, 206.26, 128/207.11, 207.13
See application file for complete search history.

(56) References Cited

U.S. PATENT DOCUMENTS 812,706 A 2/1906 Warbasse (Continued)

FOREIGN PATENT DOCUMENTS

CA 88122 11/1999

(Continued)

OTHER PUBLICATIONS

The American Heritage Dictionary, Second College Edition, 1982, 3 pages.*

(Continued)

*Primary Examiner*—Aaron J. Lewis
(74) *Attorney, Agent, or Firm*—Nixon & Vanderhye P.C.

(57) ABSTRACT

A respiratory mask assembly includes a rigid mask frame with a rim portion including a rearwardly projecting tongue and lateral flange and a cushion having a rim with a corresponding groove and a rearwardly facing shoulder. A clip in the form of a collar passes over the cushion, engaging behind the shoulder, and has securing tabs that engage recesses in the flange.

15 Claims, 19 Drawing Sheets

U.S. PATENT DOCUMENTS

| | | | | |
|---|---|---|---|---|
| 1,653,572 | A | 12/1927 | Jackson | |
| 2,029,129 | A | 1/1936 | Schwartz | |
| 2,359,506 | A | 10/1944 | Battley et al. | |
| 2,371,965 | A | 3/1945 | Lehmberg | |
| 2,823,671 | A | 2/1958 | Garelick | |
| 2,893,387 | A | 7/1959 | Gongoll et al. | |
| 2,931,356 | A | 4/1960 | Schwarz | |
| 3,189,027 | A | 6/1965 | Bartlett, Jr. | |
| 3,474,783 | A | 10/1969 | Ulmann | |
| 3,824,999 | A | 7/1974 | King | |
| 4,064,875 | A | 12/1977 | Cramer et al. | |
| 4,111,197 | A | 9/1978 | Warncke et al. | |
| 4,121,580 | A | 10/1978 | Fabish | |
| 4,164,942 | A | 8/1979 | Beard et al. | |
| 4,226,234 | A | 10/1980 | Gunderson | |
| 4,274,404 | A | 6/1981 | Molzan et al. | |
| 4,494,538 | A | 1/1985 | Ansite | |
| 4,506,665 | A | 3/1985 | Andrews et al. | |
| 4,580,556 | A | 4/1986 | Kondur | |
| 4,606,340 | A | 8/1986 | Ansite | |
| 4,622,964 | A | 11/1986 | Flynn | |
| 4,794,921 | A | 1/1989 | Lindkvist | |
| 4,807,617 | A | 2/1989 | Nesti | |
| 4,809,692 | A | 3/1989 | Nowacki et al. | |
| 4,841,953 | A | 6/1989 | Dodrill | |
| 4,870,963 | A | 10/1989 | Carter | |
| 4,875,714 | A | 10/1989 | Lee | |
| 4,898,174 | A | 2/1990 | Fangrow, Jr. | |
| 4,974,586 | A | 12/1990 | Wandel et al. | |
| 4,997,217 | A | 3/1991 | Kunze | |
| 5,003,633 | A | 4/1991 | Itoh | |
| 5,005,568 | A | 4/1991 | Loescher et al. | |
| 5,215,336 | A | 6/1993 | Worthing | |
| 5,243,971 | A | 9/1993 | Sullivan et al. | |
| 5,253,641 | A | 10/1993 | Choate | |
| 5,311,862 | A | 5/1994 | Blasdell et al. | |
| 5,398,673 | A | 3/1995 | Lambert | |
| 5,438,981 | A | 8/1995 | Starr et al. | |
| 5,501,214 | A | 3/1996 | Sabo | |
| 5,538,001 | A | 7/1996 | Bridges | |
| 5,645,049 | A | 7/1997 | Foley et al. | |
| 5,647,355 | A | 7/1997 | Starr et al. | |
| 5,676,133 | A | 10/1997 | Hickle et al. | |
| 5,709,204 | A | 1/1998 | Lester | |
| 5,724,965 | A | 3/1998 | Handke et al. | |
| 5,794,617 | A | 8/1998 | Brunell et al. | |
| 5,839,436 | A | 11/1998 | Fangrow et al. | |
| 5,860,677 | A | 1/1999 | Martins et al. | |
| 5,896,857 | A | 4/1999 | Hely et al. | |
| 5,909,732 | A | 6/1999 | Diesel et al. | |
| 5,937,851 | A | 8/1999 | Serowski et al. | |
| 5,979,025 | A * | 11/1999 | Horng | 24/459 |
| 6,082,360 | A | 7/2000 | Rudolph et al. | |
| 6,119,693 | A | 9/2000 | Kwok et al. | |
| 6,189,532 | B1 | 2/2001 | Hely et al. | |
| 6,192,886 | B1 | 2/2001 | Rudolph | |
| 6,196,223 | B1 | 3/2001 | Belfer et al. | |
| 6,240,605 | B1 * | 6/2001 | Stevens et al. | 24/546 |
| 6,250,375 | B1 * | 6/2001 | Lee et al. | 165/80.3 |
| 6,256,846 | B1 * | 7/2001 | Lee | 24/459 |
| 6,272,722 | B1 * | 8/2001 | Lai | 24/458 |
| 6,321,421 | B1 * | 11/2001 | Lim | 24/459 |
| 6,381,813 | B1 * | 5/2002 | Lai | 24/456 |
| 6,412,487 | B1 | 7/2002 | Gunaratnam et al. | |
| 6,449,817 | B1 * | 9/2002 | Hsu | 24/459 |
| 6,463,931 | B1 | 10/2002 | Kwok et al. | |
| 6,491,034 | B1 | 12/2002 | Gunaratnam et al. | |
| 6,513,206 | B1 * | 2/2003 | Banitt et al. | 24/459 |
| 6,520,182 | B1 | 2/2003 | Kwok et al. | |
| 6,532,961 | B1 | 3/2003 | Kwok et al. | |
| 6,615,832 | B1 | 9/2003 | Chen | |
| 6,796,308 | B1 | 9/2004 | Gunaratnam et al. | |
| 2002/0153012 | A1 | 10/2002 | Gunaratnam et al. | |
| 2002/0174868 | A1 | 11/2002 | Kwok et al. | |
| 2003/0005935 | A1 | 1/2003 | Kwok et al. | |
| 2004/0134497 | A1 | 7/2004 | Gunaratnam et al. | |

FOREIGN PATENT DOCUMENTS

| | | | |
|---|---|---|---|
| DE | 297 21 766 | U1 | 3/1998 |
| DE | 4 99 00 269.5 | | 1/1999 |
| EP | 1 027 905 | A3 | 8/2000 |
| ES | 145309 | | 1/2000 |
| FR | 2 691 906 | | 12/1993 |
| FR | 99/16 | | 8/1999 |
| GB | 2080119 | | 12/1998 |
| GB | 2080120 | | 12/1998 |
| GB | 2080121 | | 12/1998 |
| JP | 48-55696 | | 10/1971 |
| JP | 59-55535 | | 4/1984 |
| JP | 61-67747/86 | | 5/1986 |
| JP | 7-21058/95 | | 4/1995 |
| JP | 7-308381 | | 11/1995 |
| JP | 9-501084 | | 2/1997 |
| JP | 1105649 | | 2/1999 |
| SE | 65481 | | 8/2000 |
| WO | WO 80/01645 | | 8/1980 |
| WO | WO 87/01950 | | 4/1987 |
| WO | WO 95/04566 | | 2/1995 |
| WO | WO 98/26830 | | 6/1998 |
| WO | WO 98/48878 | | 11/1998 |
| WO | WO 99/30760 | | 6/1999 |
| WO | WO 00/38772 | | 7/2000 |

OTHER PUBLICATIONS

ResMed, Mask Systems Product Brochure, 2 pages, Sep., 1992.

Respironics, Inc. “Nasal Mask System Silicone Contour Mask” Product Instructions, 2 pages, Jun., 1997.

Japanese Office Action English Translation for JP 2000-029094, 3 pages.

ResCare Limited, “Sullivan™ Nasal CPAP System, *Nose Mask Clip—User Instructions*” May 1990, 1 page.

Respironics, Inc., “Nasal Mask System Silicone Contour Mask,” Product Instructions, 2 pages, Jun. 1997.

ResMed, Mask Systems product Brochure, 2 pages, Sep. 1992.

* cited by examiner

MASK CUSHION AND FRAME ASSEMBLY

CROSS REFERENCE TO RELATED APPLICATIONS

This application is a Divisional of U.S. application Ser. No. 10/123,484, filed Apr. 17, 2002, now now U.S. Pat. No. 6,796,308, which is a Continuation of U.S. application Ser. No. 09/501,004, filed Feb. 9, 2000, now U.S. Pat. No. 6,412,487, which is a Continuation-in-Part (CIP) of U.S. application Ser. No. 09/498,705, filed Feb. 7, 2000, now U.S. Pat. No. 6,491,034, a CIP of U.S. application Ser. No. 09/316,227, filed May 21, 1999, now U.S. Pat. No. 6,513,526; a CIP of U.S. Design application Ser. No. 29/101,860, filed Mar. 12, 1999, now U.S. Design Pat. No. D428,139; a CIP of U.S. Design application Ser. No. 29/101,861, filed Mar. 12, 1999, now U.S. Design Pat. No. D430,663; a CIP of U.S. Design application Ser. No. 29/101,862, filed Mar. 12, 1999, now U.S. Design Pat. No. D428,988; and a CIP of U.S. Design application Ser. No. 29/115,618, filed Dec. 16, 1999, now U.S. Design Pat. No. D443,355, each of which is incorporated by reference in its entirety.

FIELD OF THE INVENTION

The invention relates to a method and apparatus for connecting a nasal or full-face mask cushion to a mask frame, where the mask is suitable for the delivery of breathable gases to a patient for the treatment of sleep disordered breathing (SDB).

BACKGROUND TO THE INVENTION

Nasal and full-face masks systems suitable for the delivery of air or other breathable gases to patients for the treatment of sleep disordered breathing may include a mask (100), a forehead support (120) and headgear (140), as depicted in FIG. 1. The mask may comprise a rigid shell (160), termed a frame, and a soft portion (180), termed a cushion. The frame may be constructed from a material such as polycarbonate, forming a cavity which overlies the patient's nose and/or mouth. The soft cushion may be constructed from a material such as silicone spacing the frame away from the patient's ice to provide comfortable contact.

In the case of the Mirage® Mask (ResMed Limited), shown in FIG. 1, the headgear (140) is constructed from fabric and includes a rear portion which engages the region near the occiput of the patient, and four straps (145) which are secured to a forehead support (2 straps) and nasal mask frame (2 straps). The straps include hook and loop material, such as Velcro(™) on one side. The mask frame and forehead supports include loops through which straps can pass.

In one form of known mask, the cushion and frame are glued together, as shown in FIG. 2*a* to 2*c*. FIG. 2*c* shows a cross-section 2*c* —2*c* through FIG. 2*a*. The fame (160) includes a rim portion (200) surrounding the rear aperture of the frame. There is a corresponding rim portion (220) on the cushion (180) which fits inside the rim (200) on the frame. The two rims (200, 220) are glued together. A disadvantage with this approach is that the cushion cannot easily be removed for separate cleaning from the frame. Furthermore, there is an increased manufacturing cost since gluing requires assembly time and adhesive.

In one known mask, the Modular mask system (ResMed Limited), the frame and cushion are held together using a tongue (300) and groove (320), as depicted in FIGS. 3*a* to 3*c*. The frame (160) is generally triangular in front view. In use, the front of the free faces away from the patient and the back of the frame faces towards the patient. The rim portion (350) on the Be (160) includes an outwardly extending flange (340) and engages with a corresponding rim (360) on the cushion (180), such that the rims (350, 360) confront along a locus lying generally in the plane of the patient's face. The frame rim (350) farther includes a tongue (300) which protrudes rearwardly from the back of the frame and is received in a corresponding complementary shaped groove (320) formed in rim portion (360) of the cushion (180). In addition, the rim (350) of the frame (160) and the rim (360) of the cushion (180) include aligned slots (380) through which headgear straps (145) can pass. Hence the slots (380) and straps (145) make a contribution to holding the frame (160) and cushion (180) together, in addition to the use of the tongue (300) and groove (320).

In another known mask, a tongue and groove mechanism is used to hold the frame (160) and cushion (180) together, and the tongue (500), which is positioned on the frame (160) has an irregular cross-section, as depicted in FIG. 4*a* to 4*c*. The side (520) of the tongue (500) on the interior of the frame (160) is flat. The other side (540) of the tongue (500) has a lateral projection (560) approximately at right angles to the tongue (500). The groove (580) of the cushion (180) has a complementary shape, including a lateral recess (585) for receiving projection (560). The connection relies on the elasticity of the cushion to retain the cushion in place.

The present invention aims to provide an improved arrangement.

SUMMARY OF THE INVENTION

The present invention provides a respiratory mask assembly for delivering breathable gas to a patient, comprising (i) a substantially rigid mask frame defining a cavity with a rear opening, and a rim portion surrounding said rear opening, said rim portion including a rearwardly projecting tongue, (ii) a flexible mask cushion acting to space the mask frame away from the patient's face, said cushion having a rim portion which includes a groove receiving said projecting tongue of the mask frame, and wherein an outer surface of the cushion forms a rearwardly facing shoulder, and (iii) a clip member passing over the mask cushion, having cushion retaining means engaging behind said shoulder of the cushion and securing means which engages the mask frame so as to retain the mask cushion on the mask frame.

Preferably, the clip's securing means includes at least one securing tab which engages a respective recess in the mask frame, and more preferably on a lateral flange of rim portion of the frame.

Preferably also, the clip is formed as a collar member having a plurality of tabs angularly spaced about the collar member, and the mask frame has a respective plurality of the recesses.

BRIEF DESCRIPTION OF THE DRAWINGS

In FIGS. 6*a* to 6*f* and 7*a* to 7*e* dimensions are shown in millimeters.

DETAILED DESCRIPTION OF THE INVENTION

The method and apparatus for securing a cushion to a mask frame includes a combination of tongue and groove mechanism and a clip in the form of a collar member which passes over and engages both the cushion and the frame.

Figure 5A:
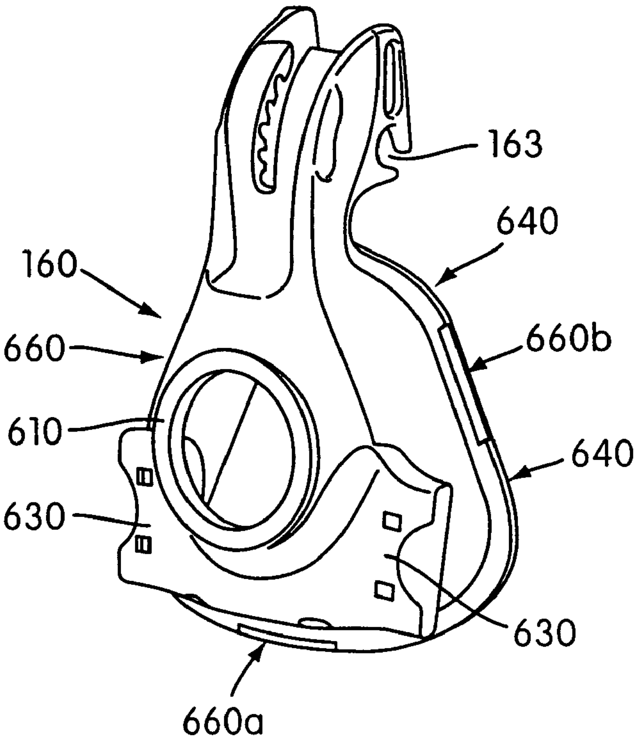
FIG. 5*a* shows a front perspective view of a nasal mask free according to an embodiment of the invention.
Figure 5B:
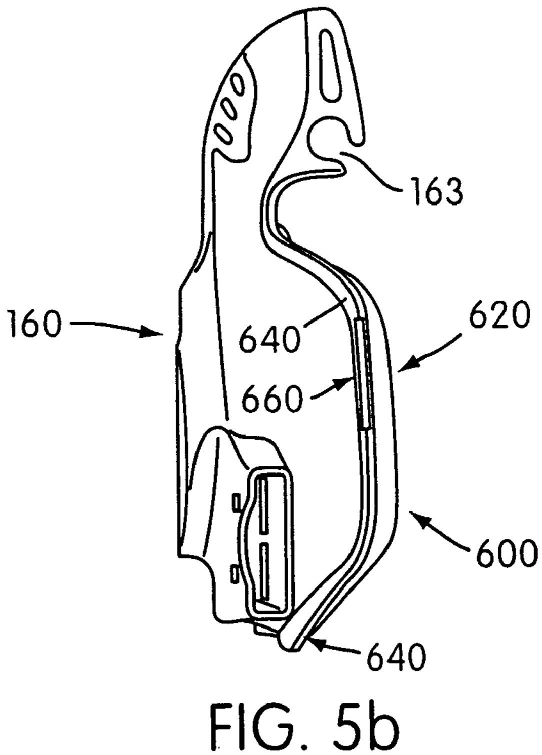
FIG. 5*b* shows a side view of the mask frame shown in FIG. 5*a*.
Figure 5C:
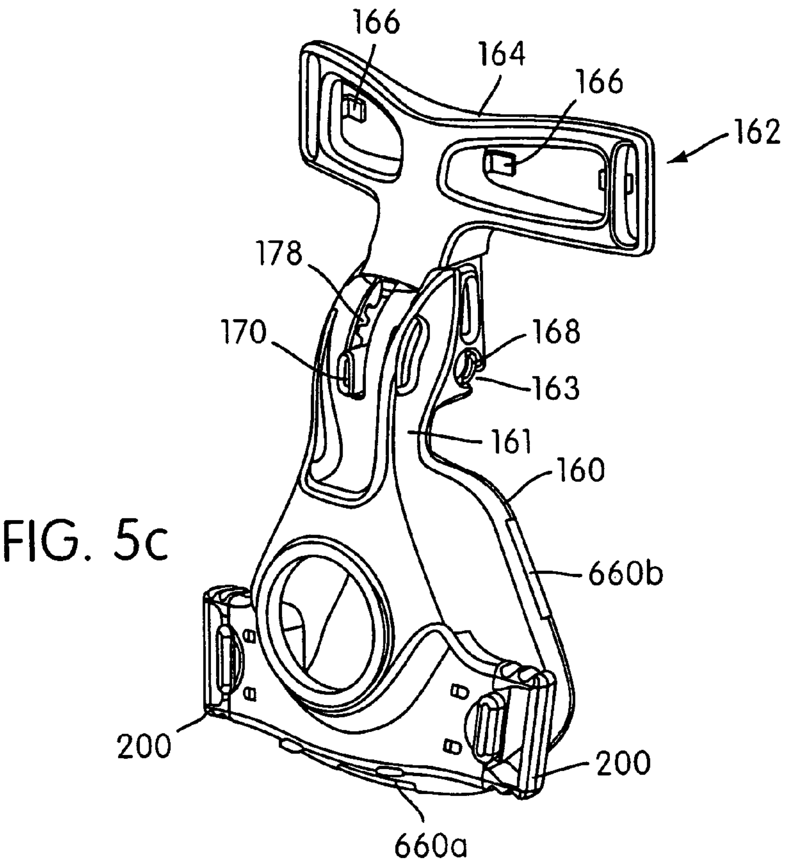
FIG. 5*c* is a front perspective view of a nasal mask frame and adjustable forehead support according to an embodiment.
Figure 5D:
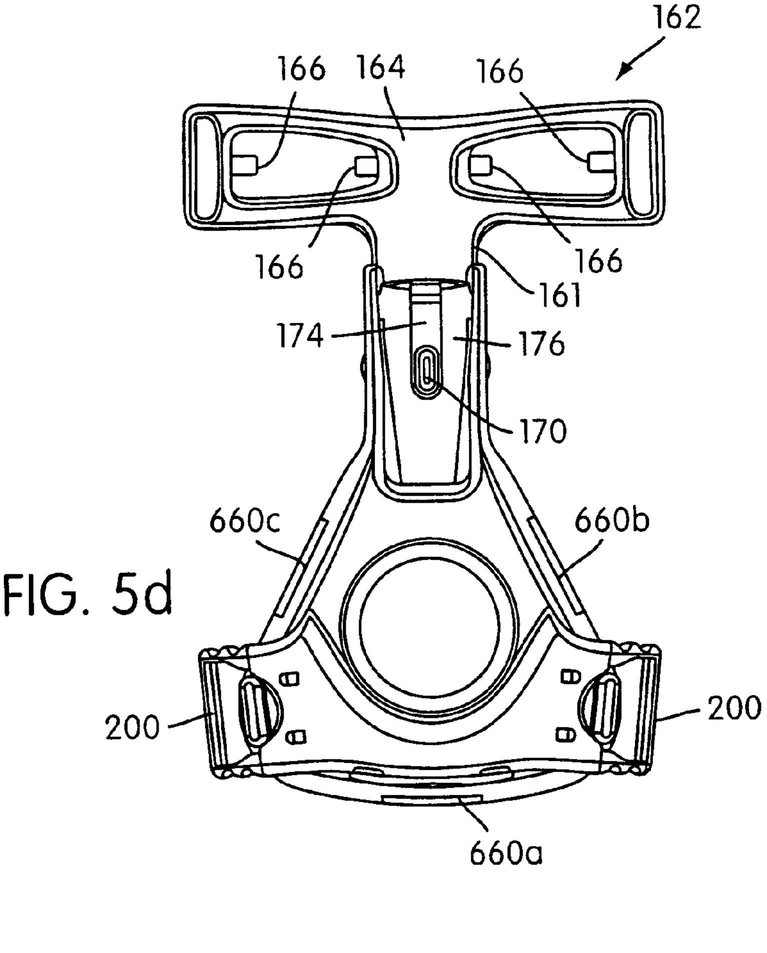
FIG. 5*d* is a front view of the embodiment of FIG. 5*c*.
Figure 5E:
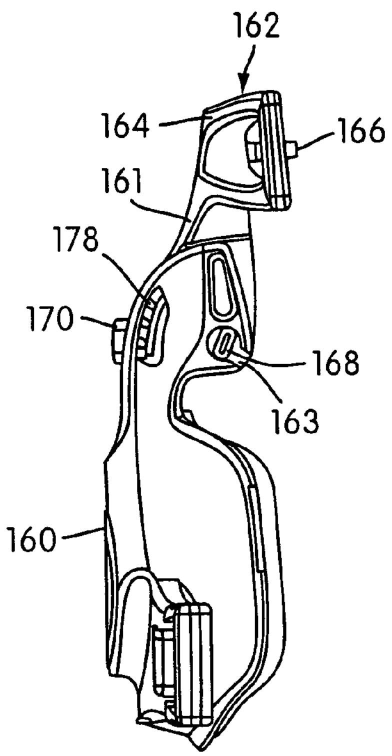
FIG. 5*e* is a side view of the embodiment of FIG. 5*c*.

A nasal mask fame including a rim portion according to an embodiment of the invention is shown in FIG. 5*a* and FIG. 5*b*. The frame (160) is constructed as a substantially rigid shell of polycarbonate or similar transparent plastics material, and incorporates a gas inlet aperture (610) for connection to a gas delivery conduit (not shown) of a patient gas delivery system.

The frame (160) is generally triangular in front view, covering the patient's nose, and defines a cavity which is open at its rear, the rear opening being surrounded by a rim portion (600) which follows a locus approximating the contours of a patient's face.

On the front surface of the frame, are strap connection points (630) for connection of the mask to patient headgear. Connectors (200) are shown in FIGS. 5*c*–5*f*.

As best seen in FIG. 5*b*, the rim portion (600) of the frame (160) includes a rearwardly projecting tongue (620) and a lateral flange (640). The tongue (620) has an approximately rectangular cross-section. The flange (640) is approximately perpendicular to the tongue (620) and also has an approximately rectangular cross-section. The flange (640) includes three recesses (660) angularly spaced about the rim. Of these, only the bottom recess (660*a*) and one side recess (660*b*) are visible in the view of the frame (160) shown in FIG. 5*a*. The recesses are of an approximately rectangular shape, formed in the front surface of flange (640) adjacent its edge.

FIGS. 5*c*–5*f* show additional views of the frame (160). As compared to FIGS. 5*a*–5*b*, FIGS. 5*c*–5*f* also show an adjustable forehead support (162) connected to the frame (160). The adjustable forehead support (162) includes a bridge portion (164) adapted to locate at least one and preferably two spaced apart pads (not shown) adapted to contact the forehead of the patient. Projection members (166) are formed on the bridge portion (164), and can be used to secure the forehead pads to the bridge portion (164).

The forehead support (162) is coupled to the frame (160) in this example using a pair of small shafts (168) formed on the forehead support (162). The frame (160) includes an extension (161) having a pair of keyed receiving slots (163) to receive the shafts (168). Adjustment is carried out by use of an actuator button (170) coupled in cantilever fashion to the end of a tab (172) formed on the forehead support (162). The actuator button (170) protrudes from the patient side of the extension (161) through a slot (174) (FIG. 5*d*) formed in the extension (161), thereby exposing the actuator button (170) to the exterior surface (176) of the extension (161), which facilitates access by the patient. The frame (160) is provided with a number of teeth (178), e.g. at least three, to enable the forehead support (162) to be positioned in a corresponding number of positions, so the mask can accommodate patients having a wide scope of facial geometries.

Figure 5F:
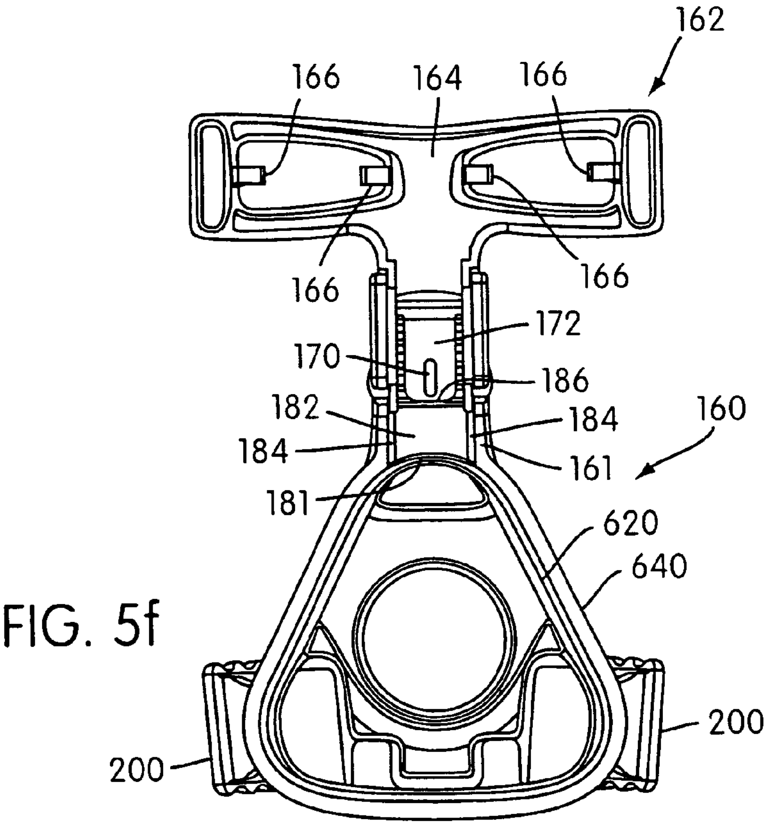
FIG. 5*f* is a rear view of the embodiment of FIG. 5*c*.

FIG. 5*f* shows that the tongue (620) and the flange (640) have a generally triangular shape. An apex (181) of the tongue (620) is provided adjacent to a point where the extension (161) extends upwardly above the main part of the frame (160). A receiving space (182) is defined in a region of the extension (161) just above the apex (181) of the tongue (620). Sidewalls (184) define the side boundaries of the receiving space (182), while the end (186) of the tab (172) defines the upper boundary of the receiving space (182). The purpose of the receiving space (182) will be described below in conjunction with FIGS. 7*a*–7*e*.

A nasal mask cushion including a rim portion (700) according to an embodiment of the invention is shown in FIGS. 6*a* to 6*f*. The front edge of the rim portion (700) has a groove (740) which is of complementary shape to and closely receives the tongue (620) of the frame (160).

The thickened rim portion (700) of the cushion has an inwards step (720) in its outer surface, forming a rearwardly facing shoulder.

Figure 6C:
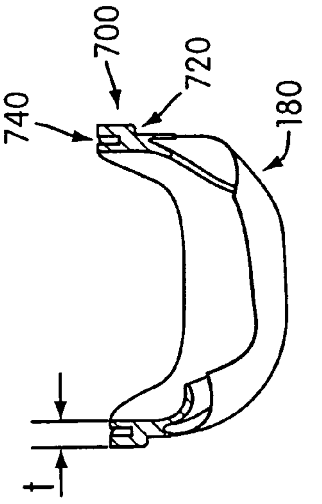
FIG. 6*c* shows a cross-section through the mask cushion shown in FIG. 6*e*.
Figure 6F:
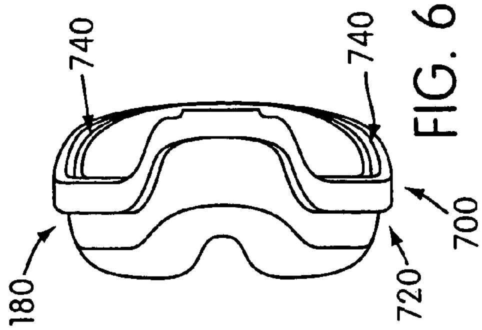
FIG. 6*f* shows a top view of the mask cushion shown in FIG. 6*e*.
Figure 6B:
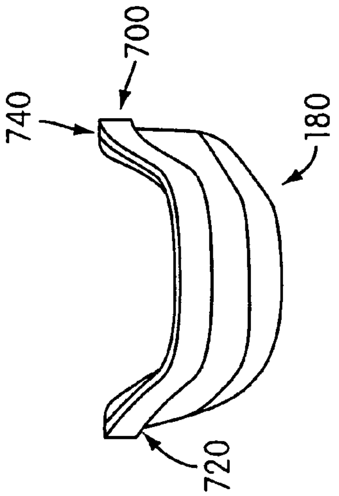
FIG. 6*b* shows a side view of the mask cushion shown in FIG. 6*e*.
Figure 6E:
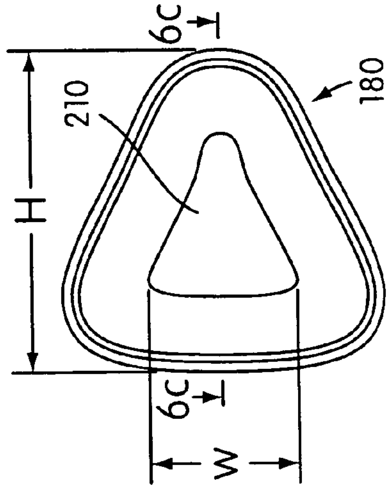
FIG. 6*e* shows a view from the patient (rear) side of the mask cushion shown in FIG. 6*a*.
Figure 6A:
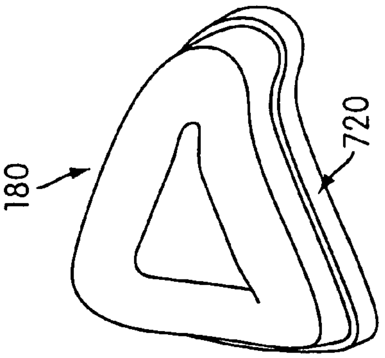
FIG. 6*a* shows a rear perspective view of a nasal mask cushion suitable for the nasal mask frame of FIGS. 5*a* and 5*b*.
Figure 6D:
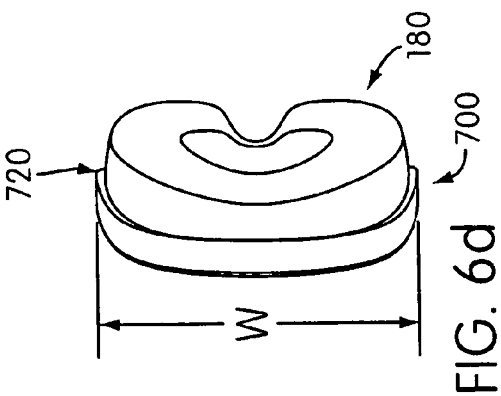
FIG. 6*d* shows a bottom view of the mask cushion shown in FIG. 6*e*.

The cushion is formed of soft material such as silicone, and projects rearwardly of the mask frame so as to space the rigid frame away from the patient's face. The width (W) of the cushion is about 71.2 mm, as shown in FIG. 6*d*. The width (W) of the aperture 210 is about 31.7 mm. The height (H) is about 72.1 mm. The height of the aperture 210 is about 36.7 mm. The thickness (t) of the lower sidewall is about 6.6 mm, as shown in FIG. 6*c*.

A clip (800) according to an embodiment of the invention, suitable for a nasal mask, is shown in FIGS. 7*a* to 7*e*. The clip is formed as a collar of a complementary shape to the rims of the mask cushion (700) and frame (600) and fits over them. The clip is constructed from polycarbonate or similar material. In the illustrated embodiment the clip (800) includes three securing tabs (820) such that inwards projections on the detents are formed as resilient detents which extend past the outer edge of flange (640) to be retained in recesses (660) on the front of the flange (640). To disengage, for example for cleaning of the mask assembly or replacement of the cushion, the detents may be forced outwardly against their natural resilience to release from the recesses (660) and ride over the cuter edge of flange (640). In other embodiments, other numbers of securing tabs may be used.

The rear of the clip has an inwards flange (840) which engages behind the shoulder (720) of the cushion so as to hold the cushion securely in position on the frame when the tabs (820) are engaged on the rim (600) of the frame.

Figure 7B:
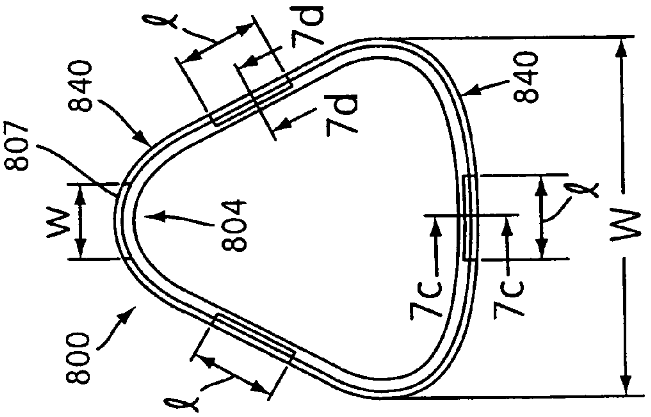
FIG. 7*b* shows a view of the clip shown in FIG. 7*a*.
Figure 7E:
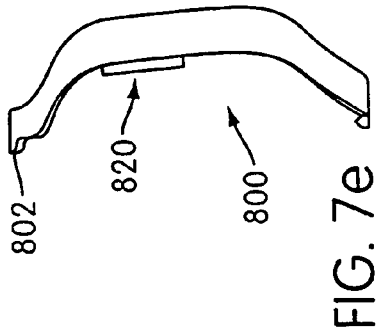
FIG. 7*e* shows a side view of the clip shown in FIG. 7*b*.
Figure 7D:
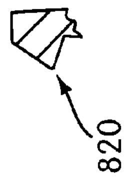
FIG. 7*d* shows an enlarged section 7*d*—7*d* through the clip in the position indicated in FIG. 7*b*.
Figure 7A:
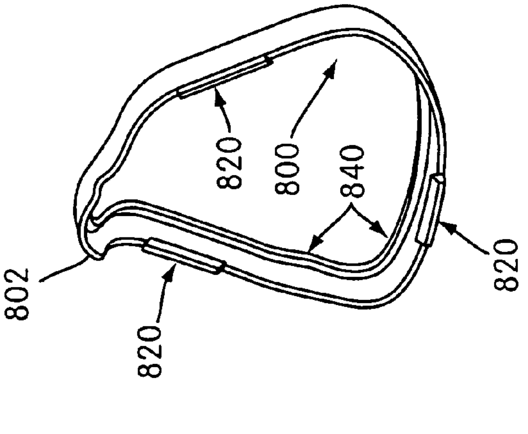
FIG. 7*a* shows a perspective view of a clip suitable for the nasal mask frame of FIGS. 5*a* and 5*b* and the nasal mask cushion of FIGS. 6*a* to 6*f*.
Figure 7C:
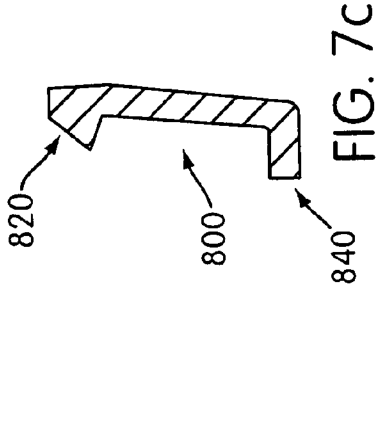
FIG. 7*c* shows an enlarged section 7*c*—7*c* through the clip in the position indicated in FIG. 7*b*.
Figures 8A, 8B:
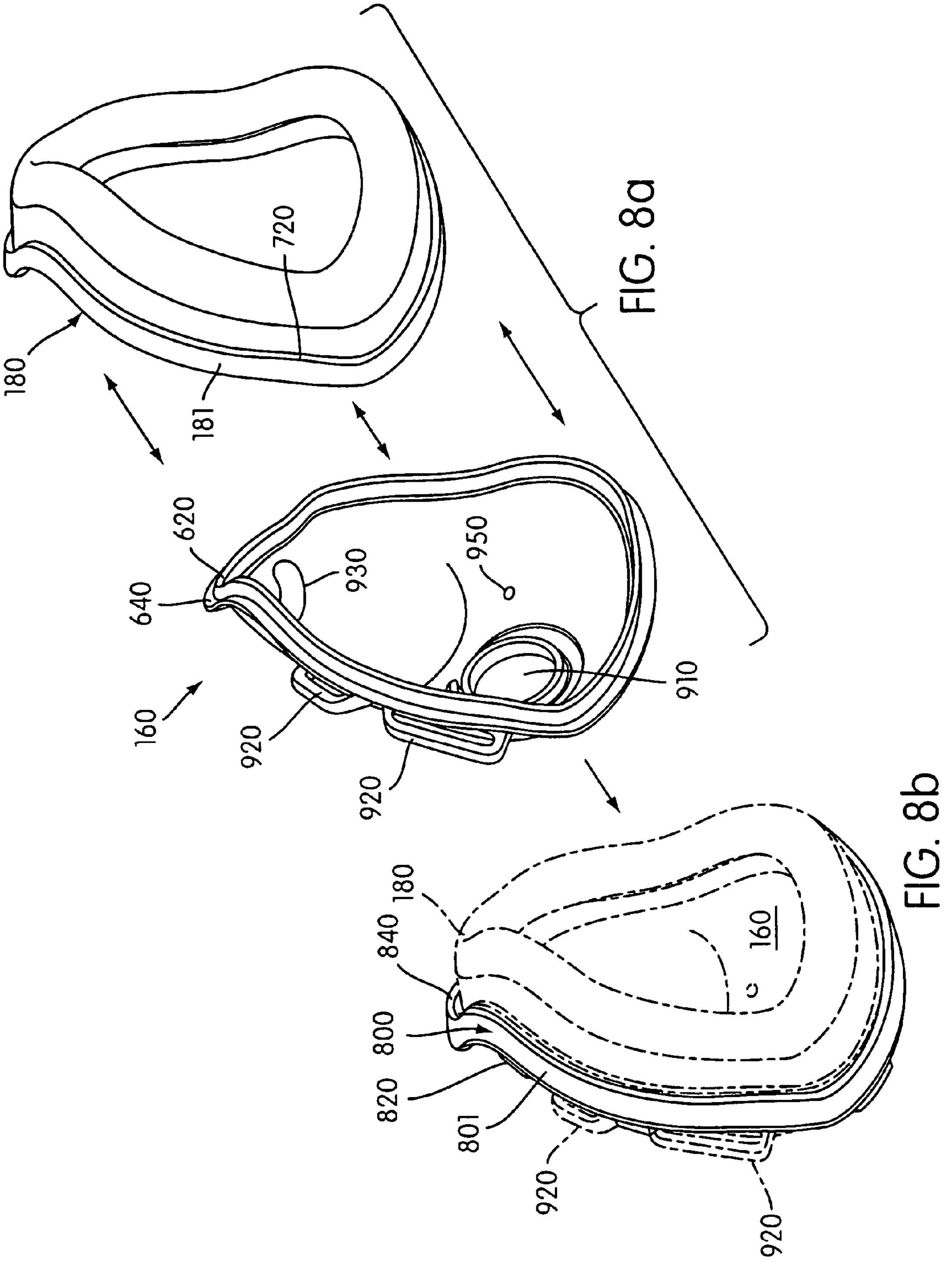
FIG. 8*a* is a rear perspective exploded view illustrating the cushion and frame according to a full mask embodiment.
FIG. 8*b* is an assembled view of the cushion and frame of FIG. 8*a*, along with the clip.

Furthermore, the clip (800) includes a guide projection (802) located at an apex (804) of the clip (800), as shown in FIGS. 7*a*, 7*b* and 7*e*. The projection (802) is positioned diametrically across from the lowermost securing tab (820), as best seen in FIG. 7*b*. The projection (802) has an arcuate shape that generally matches the curve of the clip (800) at the apex (804) thereof.

As shown in FIG. 7*b*. the length (l) of each of the securing tabs is about 18.0 mm. The width (w) of the guide projection (802) is about 15.5 mm, and the width (W) of the base of the clip (800) is about 73.83±0.5 mm.

The guide projection (802) helps guide the clip (800) into place when the clip (800) is secured to the frame (160). In this context, the guide projection (802) is not shown as including inwardly facing detents, which distinguish the guide projection (802) from the securing tabs (820), which have inwardly facing detents. In particular, the guide projection (802) is intended to be received within the receiving space (182), which is shown in FIG. 5*f*. The guide projection (802) has a shape that is complementary to the shape of the apex (181) of the tongue (620) of the frame (160). The width (w) of the guide projection (802) is dimensioned such that it fits between sidewalls (184) of the extension (161).

Figures 14A, 14B:
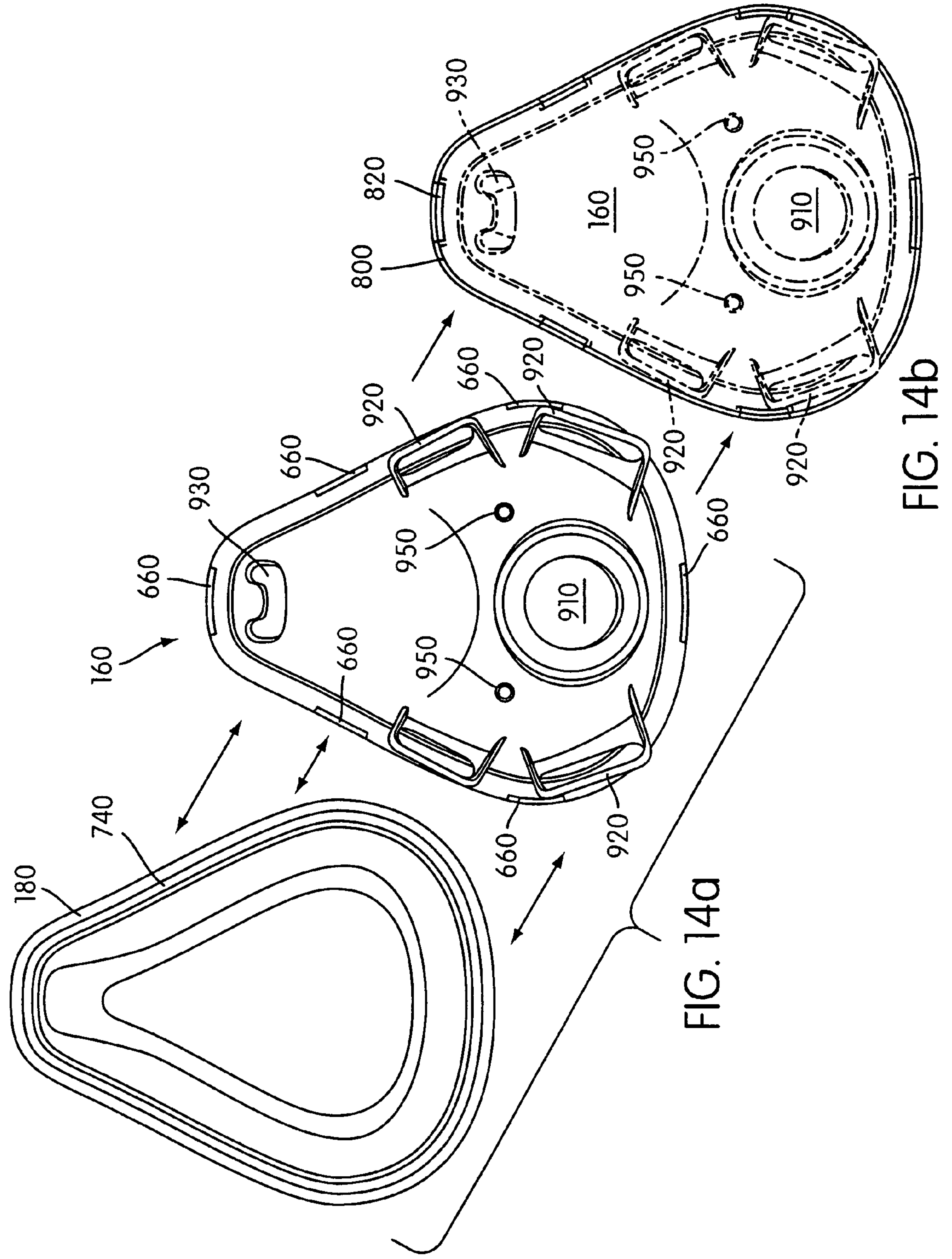
FIG. 14*a* is an exploded front view of the frame and cushion according to the full face mask.
FIG. 14*b* is an assembled view of the cushion and frame, along with the clip.
Figure 15:
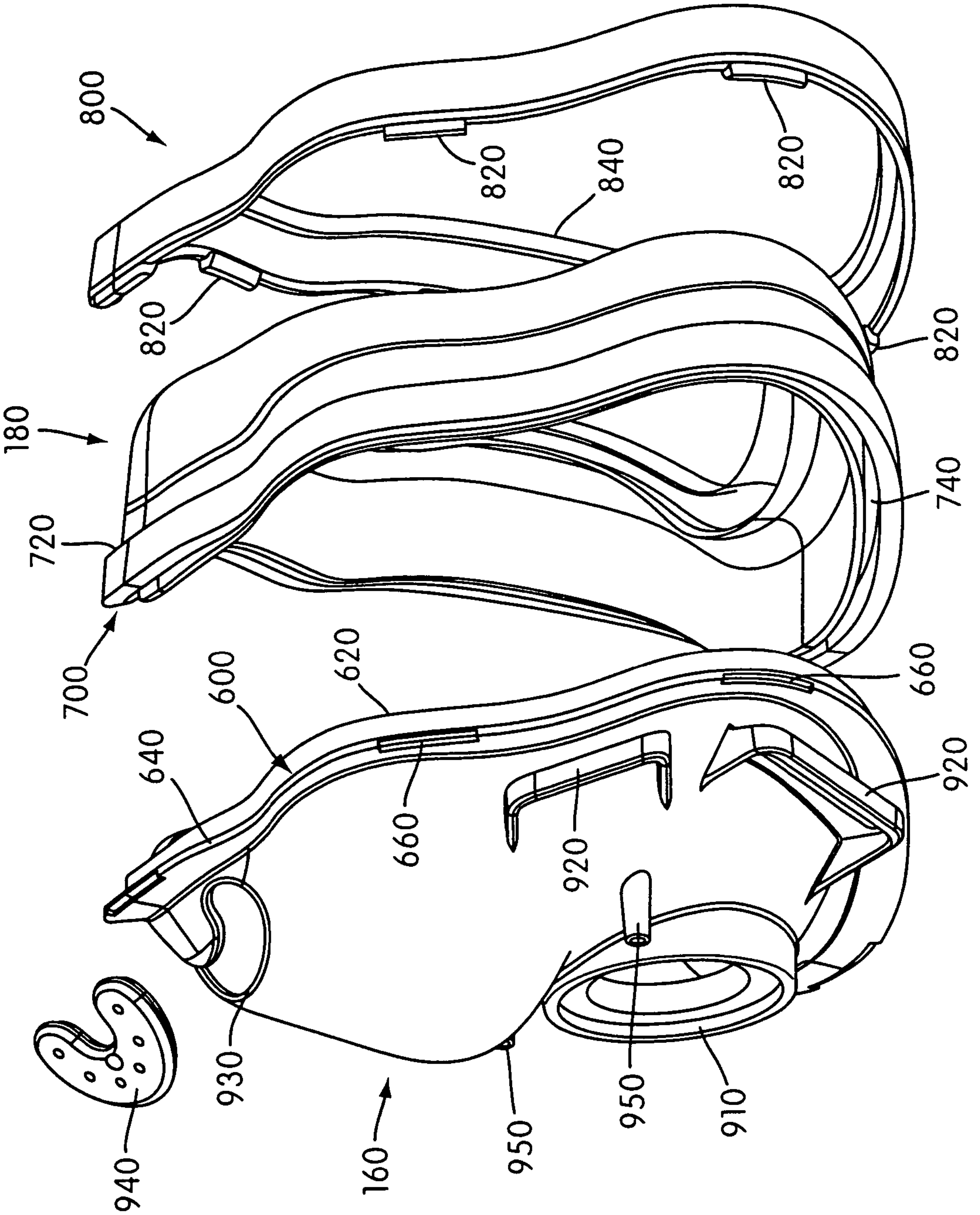
FIG. 15 is an exploded view of an embodiment of the invention as a full-face mask.
Figure 16A:
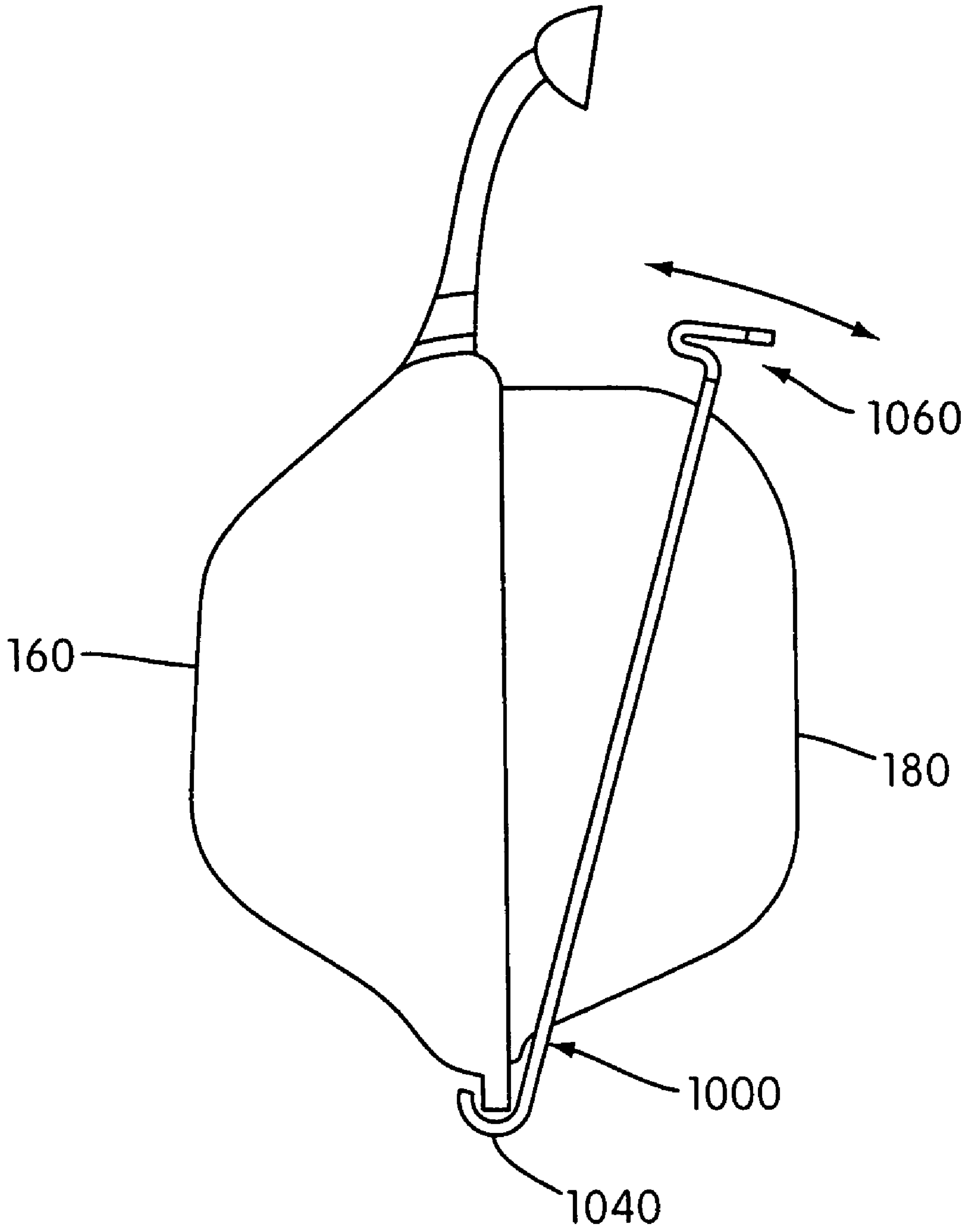
FIG. 16*a* is a schematic side view of an embodiment employing an alternative clip arrangement.
Figure 16B:
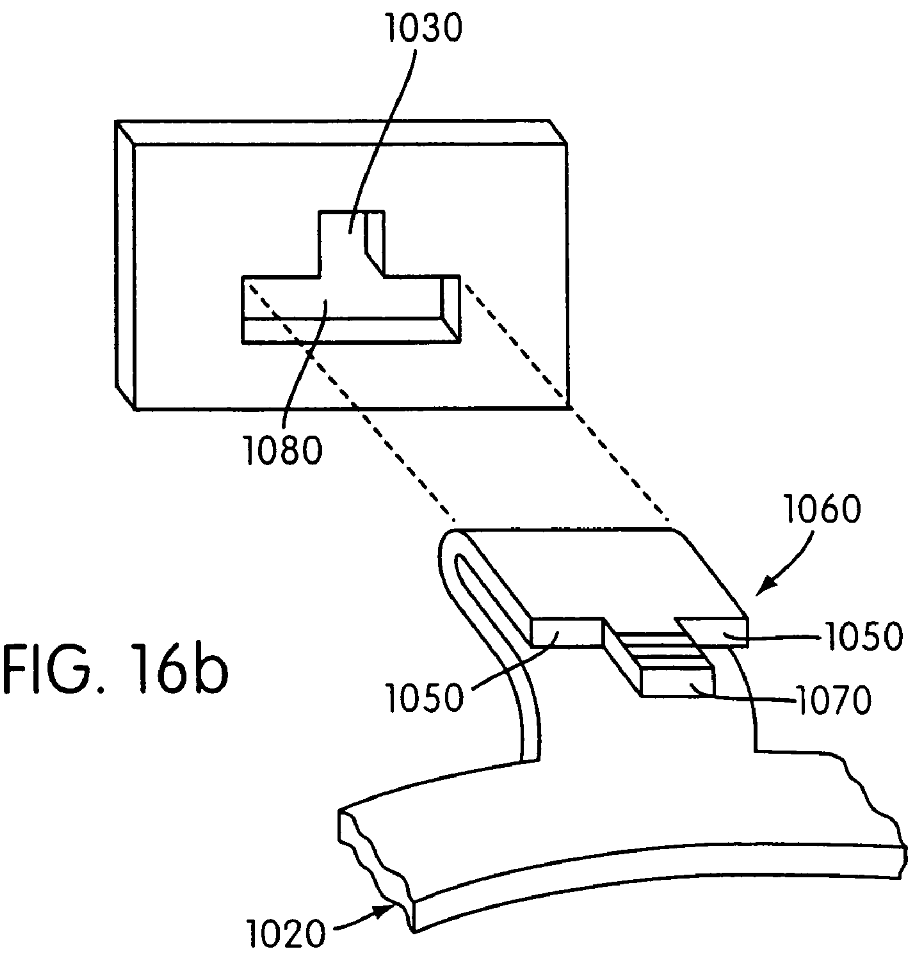
FIG. 16*b* is a perspective view of engagement of the clip with the mask frame.
Figure 16C:
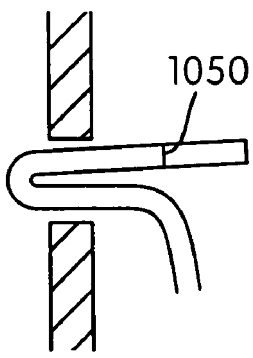
FIGS. 16*c* and 16*d* are side views showing clipping of the tab into the slot on the mask frame.
Figure 16D:
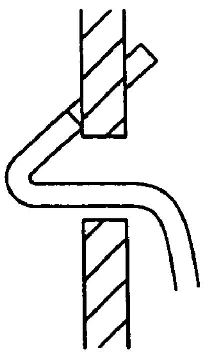

The invention is also suitable for a full-face mask system. FIGS. 8*a*–15 show several exploded views of a Mirage® full-face mask which includes an embodiment of the invention, including a mask frame (160), cushion (180) and clip (800). While FIGS. 8*a*, 9*a*, 10*a*, 11*a*, 12*a*, 13*a* and 14*a* show an exploded view of the frame (160) and the cushion (180), FIG. 15 shows an exploded view including the clip (800) as well. FIGS. 8*b*, 9*b*, 10*b*, 11*b*, 12*b*, 13*b* and 14*b* show the assembled view of the cushion, clip and frame, with the cushion and frame shown in phantom and the clip shown in solid lines. The clip (800) in FIG. 8*b* can be seen to overlie the cushion (180) since a sidewall (801) of the clip (800) instead of the sidewall (181) of the cushion (180) is visible. In addition, at least one of the securing tabs (820) can be seen. In FIGS. 9*a*–12*a* and 14*a*, recesses (660) can be seen on the frame (160), and FIGS. 9*b*–12*b* and 14*b* show the securing tabs (820) which engage with the recesses (660). FIG. 14*b* in particular shows that the clip (800) completely surrounds the frame (160), and each of the securing tabs (820) is positioned within respective recesses (660). FIG. 14*b* also shows that the recesses (660) are slightly larger than the securing tabs (820) in length so as to allow for a small degree of misalignment, to facilitate assembly. The frame is adapted to cover both the mouth and nose region of the patient's face, and includes a gas inlet aperture (910), connection points (920) for headgear straps, an aperture (930) for receiving an air vent (940) (FIG. 15) and ports (950).

The interengagement of the clip (800) and the respective rim portions (600), (700) of the frame (100) and cushion (180) are similar in principle and construction to those described above with reference to FIGS. 5*a* to 5*f* and 7*a* to 7*e*, except there are six angularly spaced tabs (820) and the respective recesses (660). As in the nasal mask assembly, the rim portion (600) of the frame includes a tongue (620) and a lateral flange (650) with recesses in its front surface adjacent its edge, the rim portion (700) of the cushion having a complementary groove (740) and rear shoulder surface (720), and the clip having a flange (840) and securing tabs (820) generally as described above for the nasal mask assembly.

FIGS. 16*a* to 16*d* illustrate an alternative clipping arrangement. The clip (1000) is again formed generally as a collar, with a rear flange (1020) for engaging the shoulder of the cushion as previously described.

At the base of the clip is a securing hook (1040) which hooks over and engages behind the lateral flange of the mask frame (160), allowing the clip to pivot.

Figures 9A, 9B:
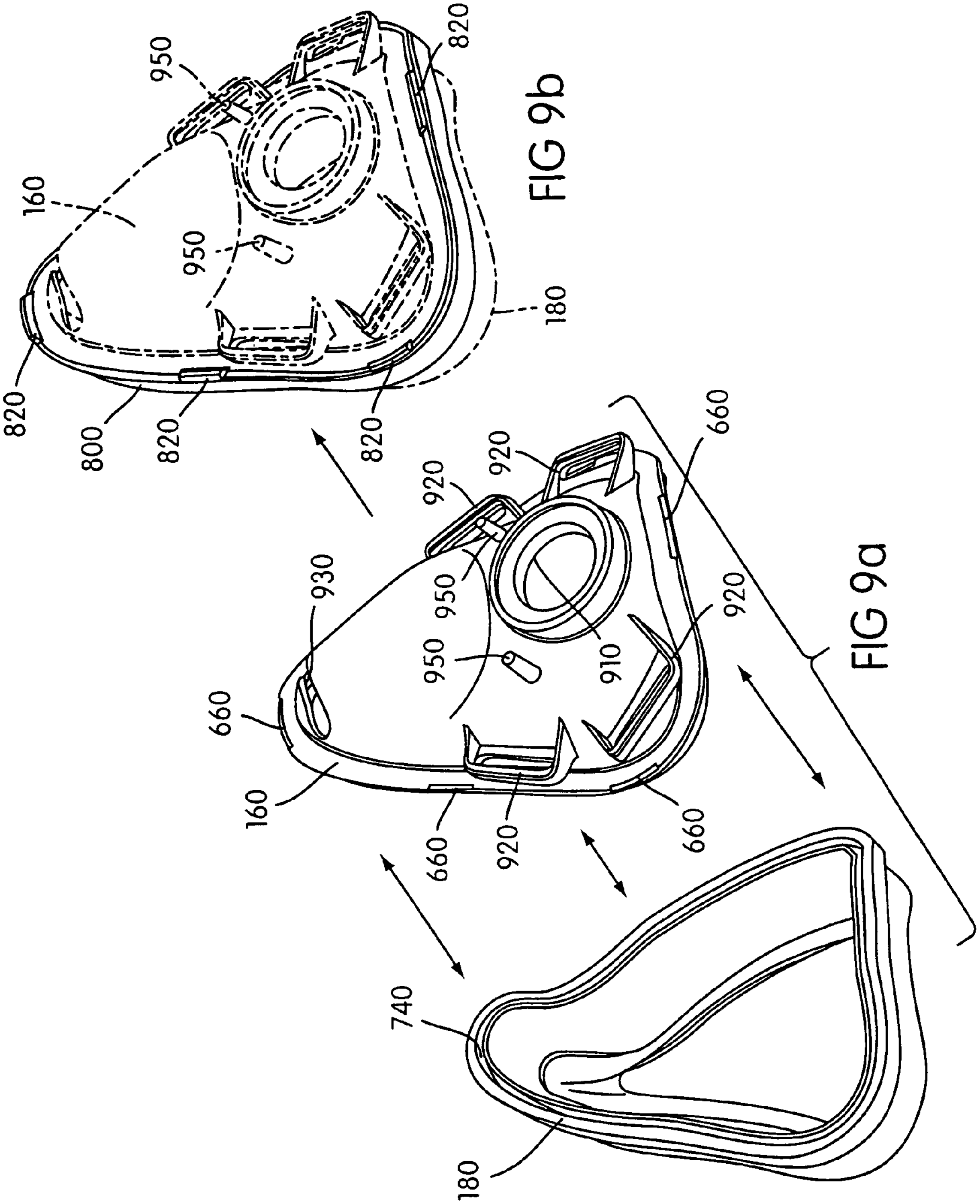
FIG. 9*a* is a front perspective exploded view illustrating the cushion and frame according to the full face mask embodiment.
FIG. 9*b* is an assembled view of the cushion and frame, along with the clip.
Figures 10A, 10B:
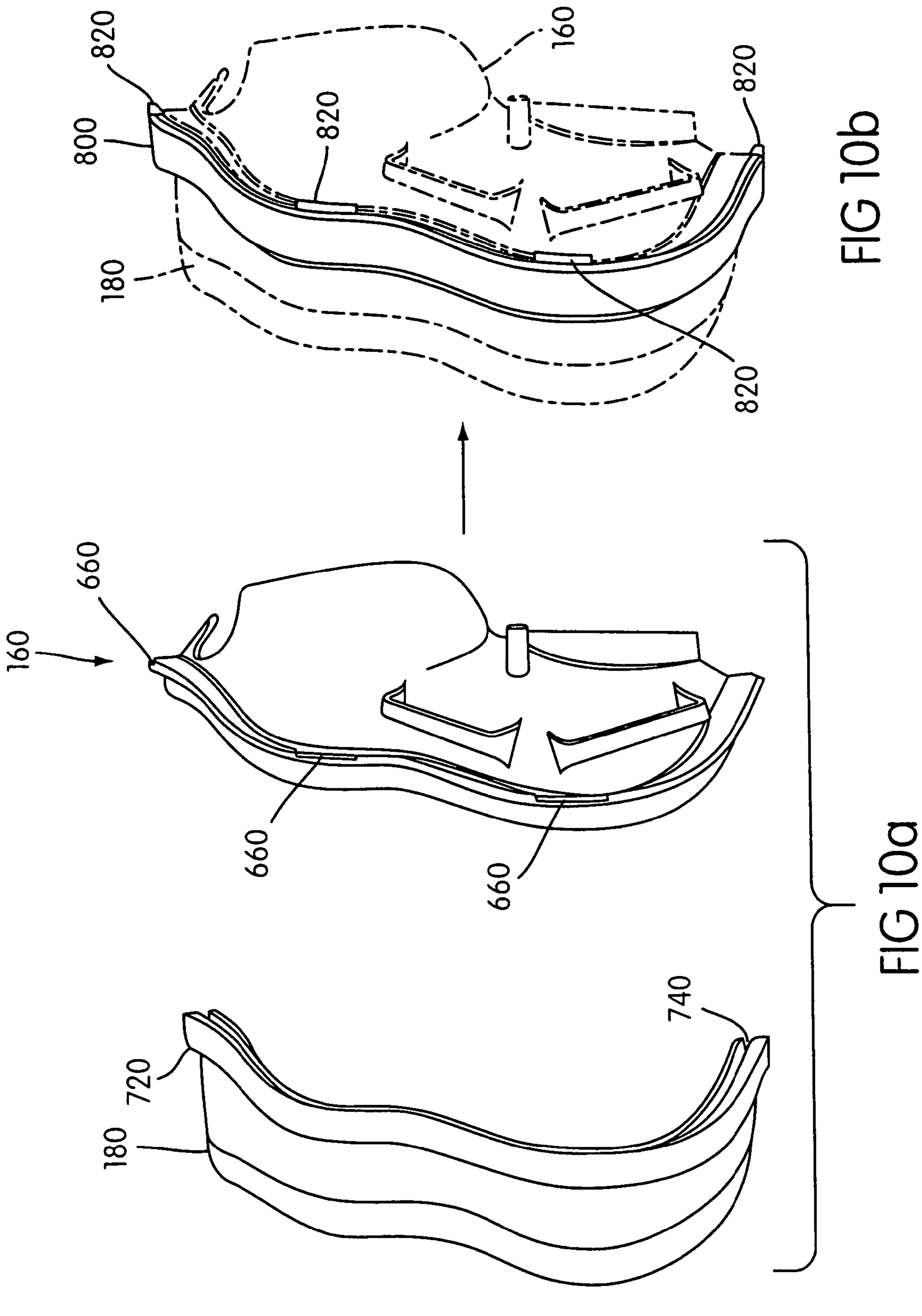
FIG. 10*a* is an exploded side view of the cushion and frame according to the full face mask embodiment.
FIG. 10*b* is an assembled view of the cushion and frame, along with the clip.
Figure 11B:
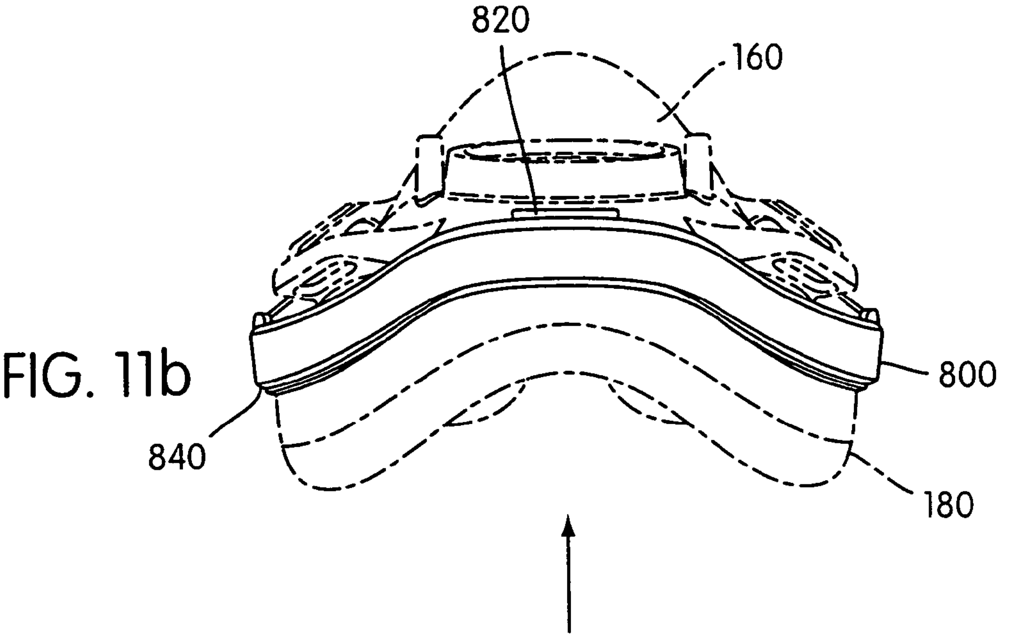
FIG. 11*b* is an assembled view of the cushion and frame, along with the clip.
Figure 11A:
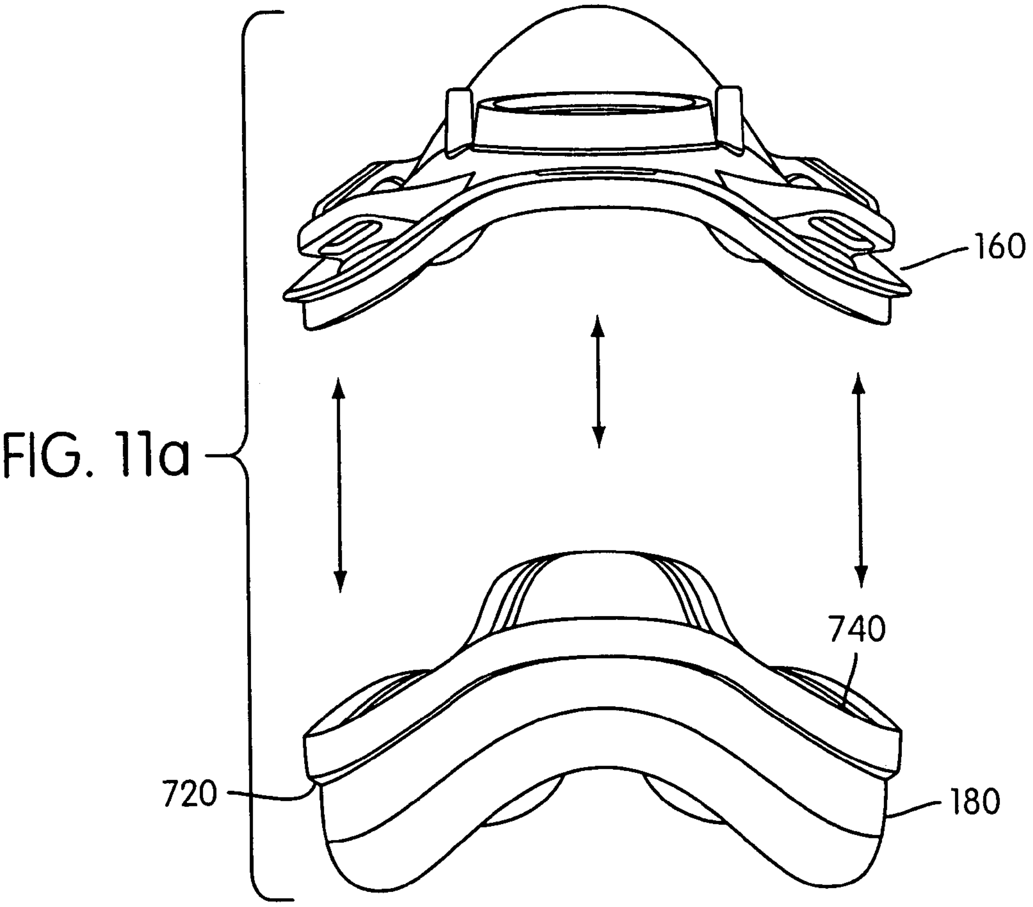
FIG. 11*a* is an exploded bottom view of the frame and cushion according to the full face mask.
Figure 12B:
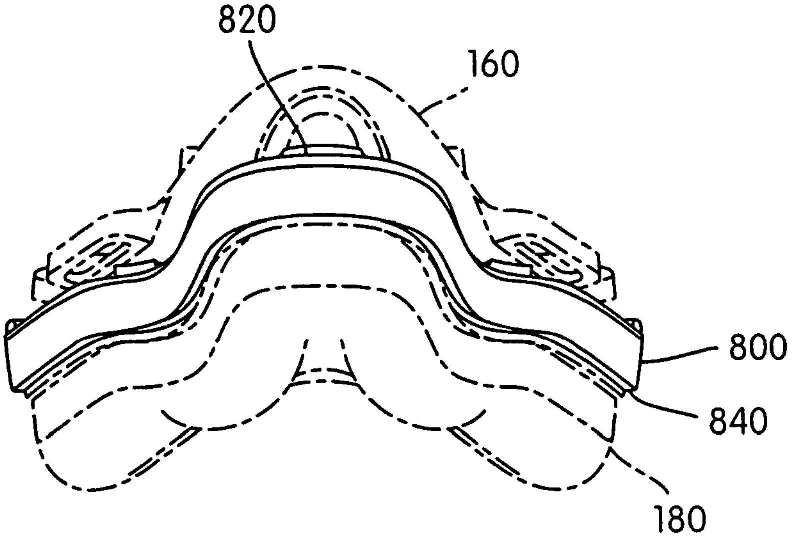
FIG. 12*b* is an assembled view of the cushion and frame, along with the clip.
Figure 12A:
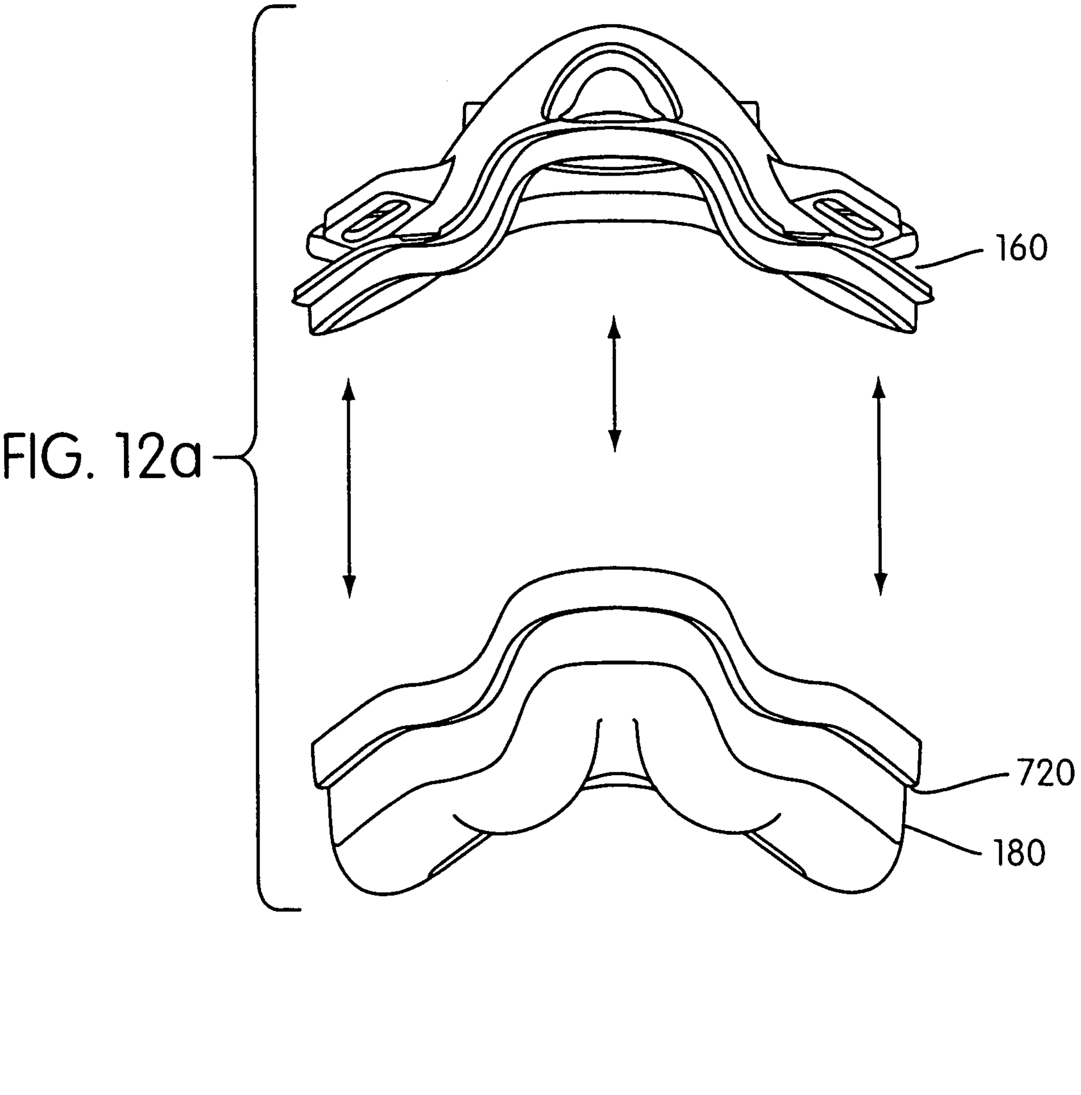
FIG. 12*a* is an exploded top view of the frame and cushion according to the full face mask.
Figures 13A, 13B:
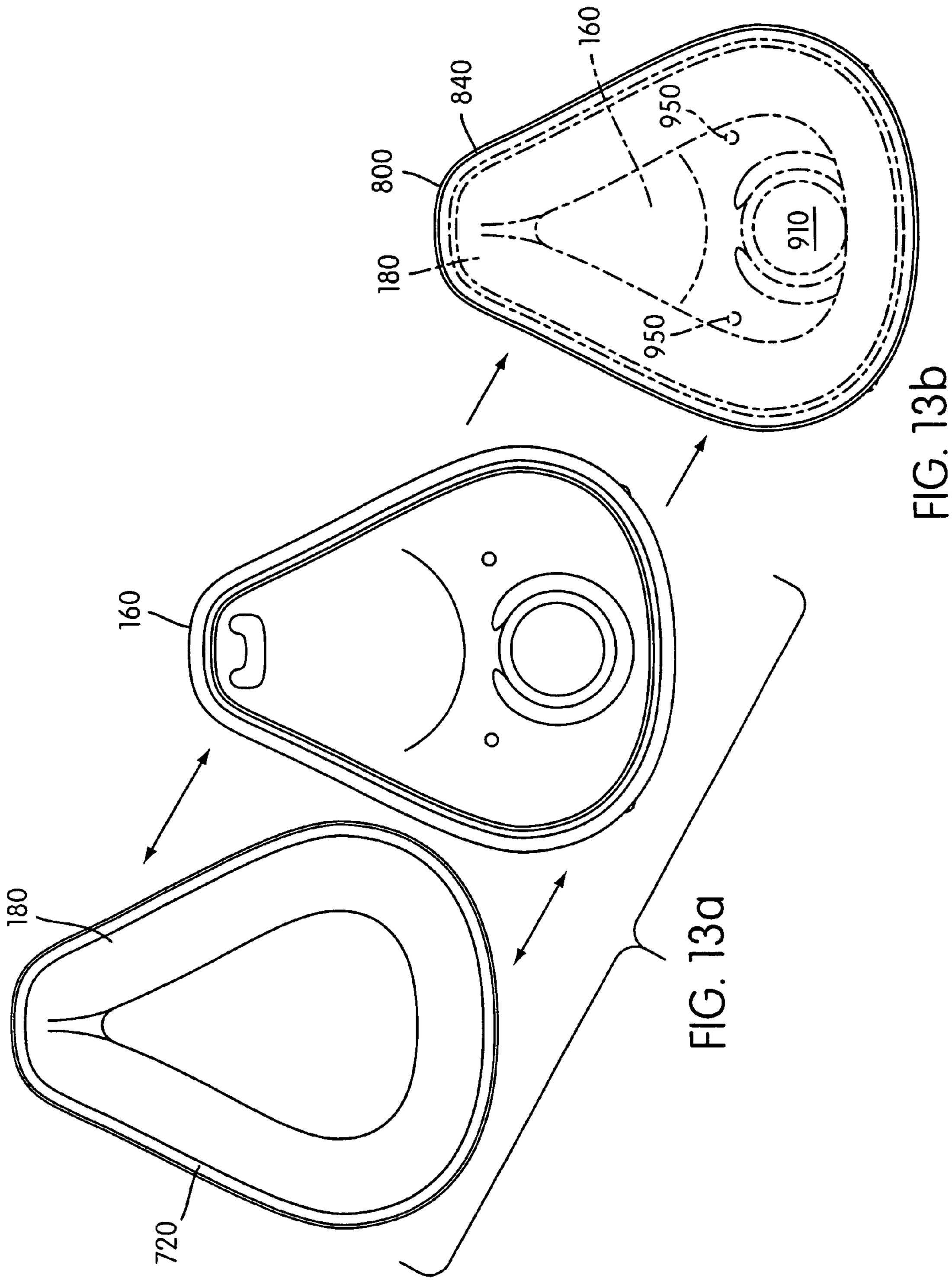
FIG. 13*a* is an exploded rear view of the frame and cushion according to the full face mask.
FIG. 13*b* is an assembled view of the cushion and frame, along with the clip.

At the top of the clip is a resilient detent arrangement (1060), adapted for engagement with an inverted T-shaped slot (1080) on the upper extension of the mask frame (160) as best shown in FIGS. 9*a* to 9*c*.

As shown, the detent is formed as a resilient U-shape with rearwardly facing shoulders (1050) either side of a narrow tab (1070). In use, the clip is pivoted to force the U-shaped detent through the wide part of the T-slot (1080), until the shoulders (1050) clear the rear surface of the slot. The resilience of the detent then forces tab (1070) into the leg (1030) of the T-slot, to retain the clip in position. To disengage the clip, the tab (1070) is depressed to allow the detent to pass back through the slot.

Figure 1:
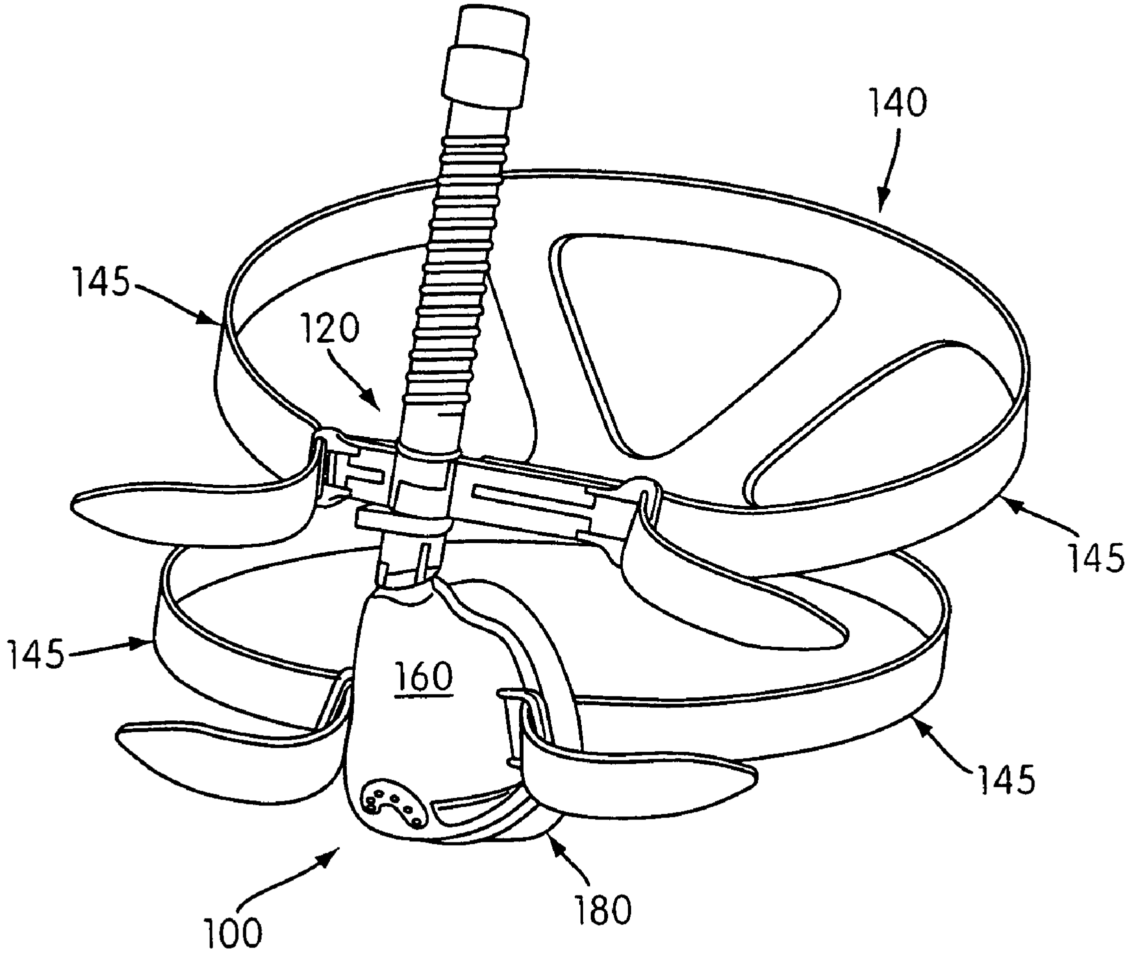
FIG. 1 shows the prior art Mirage® nasal mask system including mask frame, cushion, headgear and forehead support.
Figure 2A:
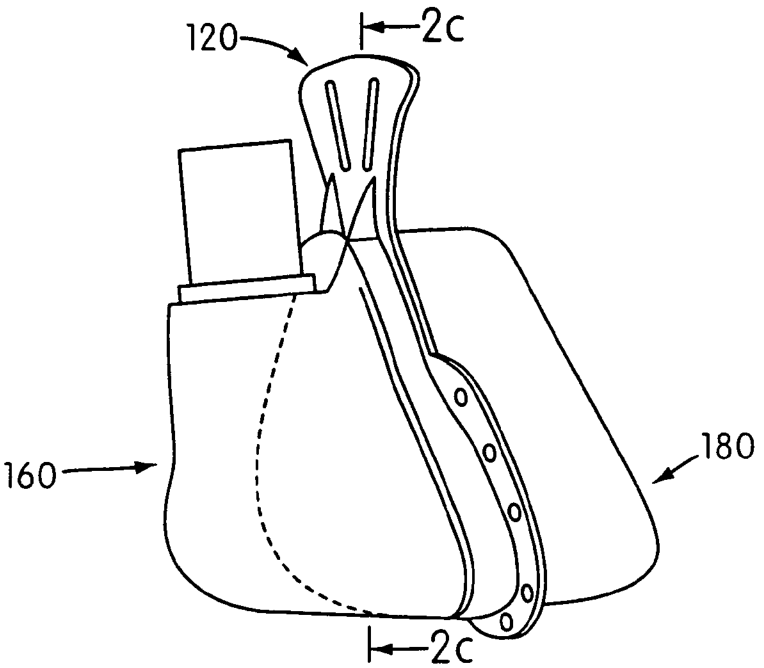
FIG. 2*a* shows a perspective view of a form of prior art mask fame and cushion, which are glued together
Figure 2B:
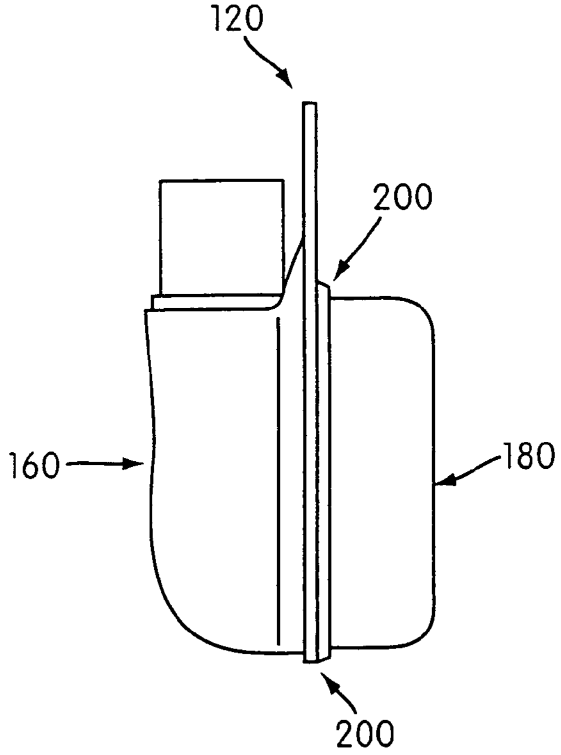
FIG. 2*b* shows a side view of the mask shown in FIG. 2*a*.
Figure 2C:
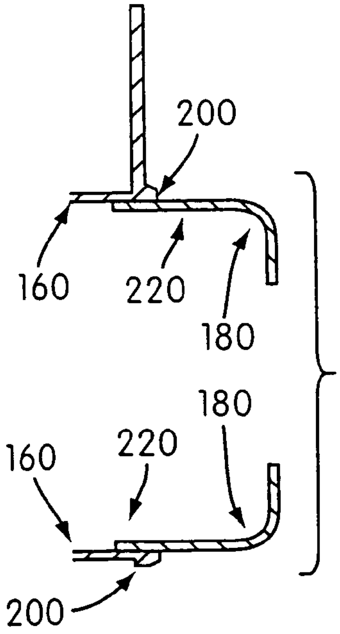
FIG. 2*c* shows a cross-sectional view of the mask shown in FIG. 2*a*.
Figure 3A:
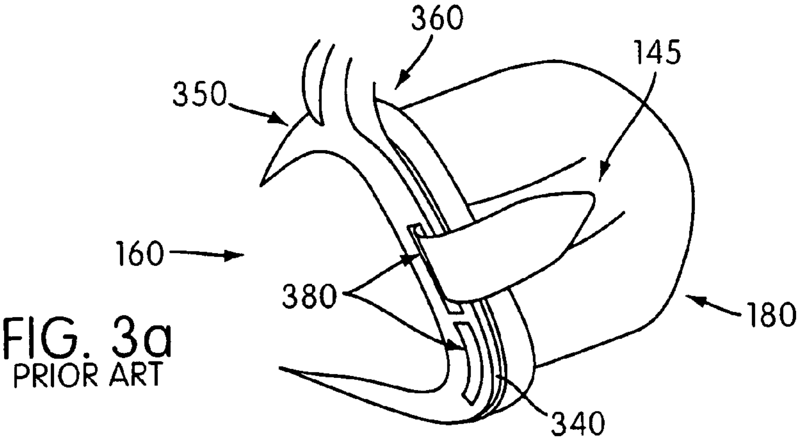
FIG. 3*a* shows a perspective view of the mask frame and cushion and strap of the prior art ResMed Modular Mask System.
Figure 3B:
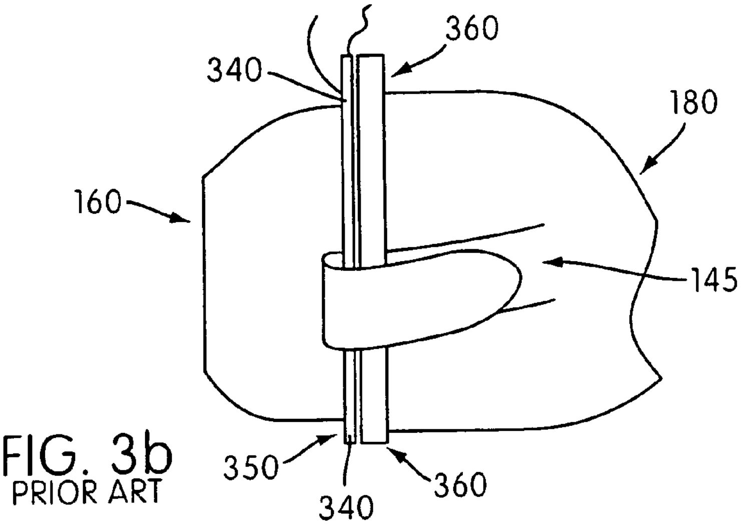
FIG. 3*b* shows a side view of the mask shown in FIG. 3*a*.
Figure 3C:
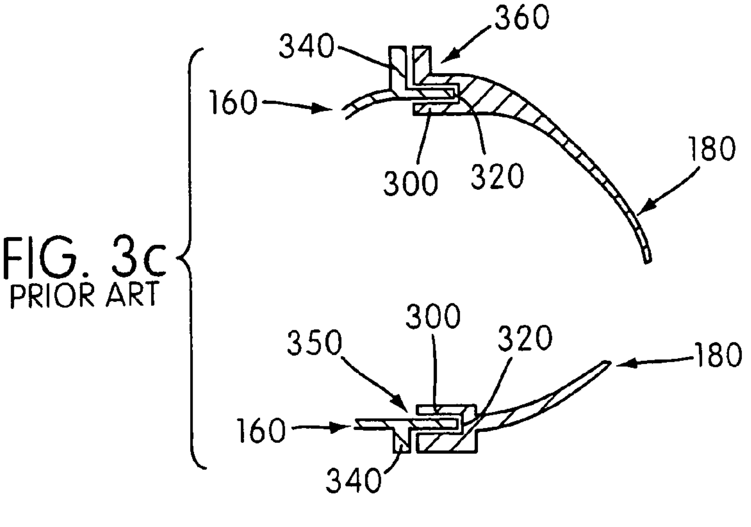
FIG. 3*c* shows a cross-sectional view of the mask shown in FIG. 3*a*.
Figure 4A:
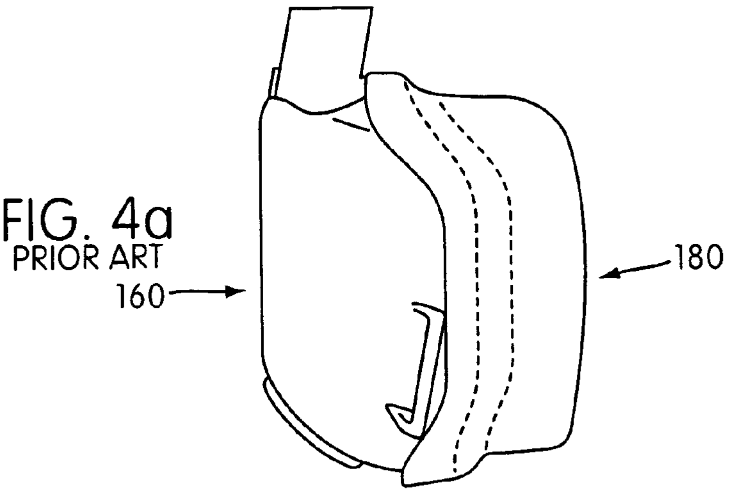
FIG. 4*a* shows a side view of a prior art mask frame and cushion incorporating a tongue and groove mechanism with an irregular cross-section.
Figure 4B:
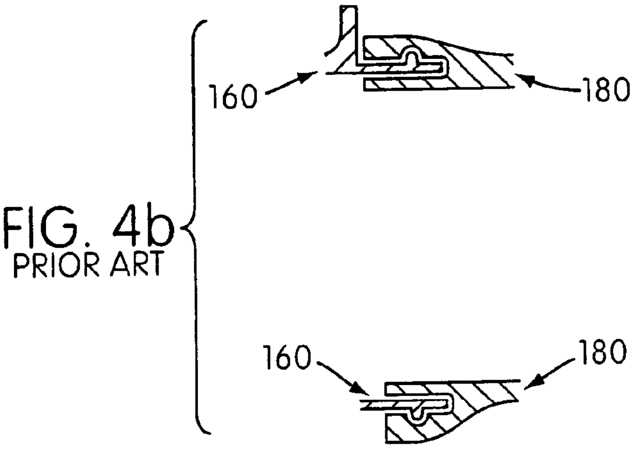
FIG. 4*b* shows a cross-sectional detail the mask shown in FIG. 4*a* where the cushion is secured to the frame.
Figure 4C:
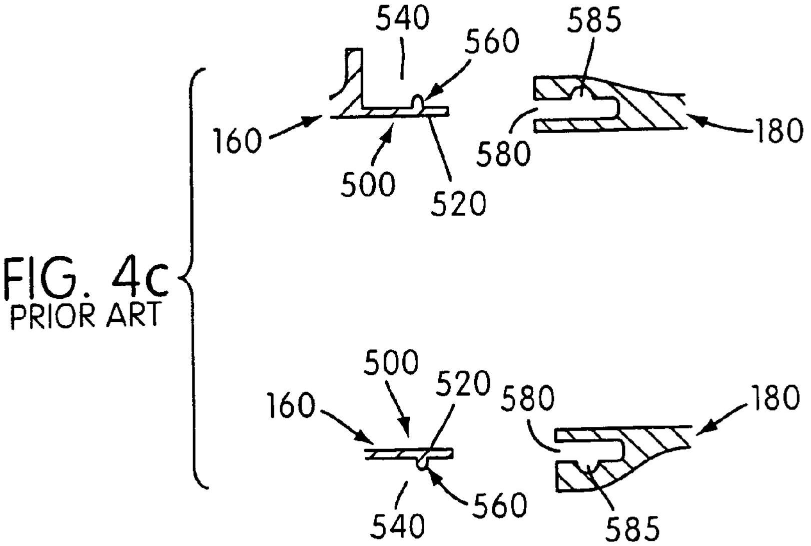
FIG. 4*c* shows a similar cross-sectional detail of the mask shown in FIG. 4*a* where the cushion is not secured to the frame.

In an unillustrated embodiment of the invention, the tongue and groove of the frame and cushion have an irregular cross-section, for example as shown in FIGS. 4*a* to 4*c*.

Although the invention has been described with reference to particular embodiments, it is to be understood that these embodiments are merely illustrative of the application of the principles of the invention. Numerous modifications may be made in the illustrative embodiments of the invention and other arrangements may be devised without departing from the spirit and scope of the invention.

What is claimed is:

1. A clip assembly for retaining a mask cushion to a generally triangular mask frame having a base side, the clip assembly including a main body having a generally triangular shape, the main body including a hook adapted to be releasably engaged with the base side of the frame and allowing the clip to pivot relative to the base, the main body further including a tab adapted for engagement with a slot located in the frame upon pivoting of the hook with respect to the frame.

2. A clip as claimed in claim 1, further including a rear flange to engage a shoulder of a cushion.

3. A clip as claimed in claim 1, wherein the clip assembly is configured to be selectively engageable with the mask cushion.

4. A clip as claimed in claim 1, wherein the hook and tab are formed as an integral one-piece unit.

5. A clip assembly as claimed in claim 1, wherein the main body is made of polycarbonate.

6. A clip assembly as claimed in claim 1, wherein the hook is open ended.

7. A mask assembly comprising:

a generally triangular mask frame having a base side;

a mask cushion provided to the frame; and a clip assembly for retaining the mask cushion to the generally triangular mask frame, the clip assembly including a main body having a generally triangular shape matching the shape of the cushion, the main body having a hook adapted to be releasably engaged with the base side of the frame and allowing the clip to pivot relative to the base, the main body further including a tab adapted for engagement with a slot located in the frame upon pivoting of the hook with respect to the frame to thereby ensure sealing engagement between the frame and cushion.

8. A mask assembly as claimed in claim 7, further including a rear flange to engage a shoulder of the cushion.

9. A mask assembly as claimed in claim 7, wherein the clip assembly is selectively engageable with the mask cushion.

10. A mask assembly as claimed in claim 7, wherein the hook and tab are formed as an integral one-piece unit.

11. A mask assembly as claimed in claim 7, wherein the main body is made of polycarbonate.

12. A mask assembly as claimed in claim 7, wherein the hook is open ended.

13. A clip assembly for retaining a mask cushion to a generally triangular mask frame having a base side, the clip assembly including a generally triangular shaped main body defining a base portion corresponding to a base portion of the frame and two side portions forming an apex, the main body including a hook provided to the base of the main body and adapted to be releasably engaged with the base side of the frame and allowing the clip to pivot relative to the base, the clip assembly further including a tab having a distal end, a proximal end and a tab shoulder oriented to face generally towards the cushion and outward of the main body, the distal end of the tab being configured to protrude through a slot located in the frame upon pivoting of the hook with respect to the frame so as to locate the tab shoulder against the frame.

14. A clip assembly as claimed in claim 13, wherein the hook is an open-ended hook.

15. A clip assembly as claimed in claim 13, wherein the main body is made of polycarbonate.

* * * * *